US011590105B2

(12) United States Patent
Mitidieri et al.

(10) Patent No.: US 11,590,105 B2
(45) Date of Patent: Feb. 28, 2023

(54) INTRATHECAL ADMINISTRATION OF LEVETIRACETAM

(71) Applicant: Sintetica S.A., Mendrisio (CH)

(72) Inventors: Augusto Mitidieri, Lugano (CH); Elisabetta Donati, Mendrisio (CH); Clara Bianchi, Torno (IT); Barbara Piccagli, Lugano (CH)

(73) Assignee: Sintetica S.A., Mendrisio (CH)

( * ) Notice: Subject to any disclaimer, the term of this patent is extended or adjusted under 35 U.S.C. 154(b) by 4 days.

(21) Appl. No.: 16/991,112

(22) Filed: Aug. 12, 2020

(65) Prior Publication Data

US 2021/0046047 A1 Feb. 18, 2021

Related U.S. Application Data

(60) Provisional application No. 62/886,706, filed on Aug. 14, 2019.

(51) Int. Cl.
| | | |
|---|---|---|
| *A61K 31/4015* | (2006.01) | |
| *A61K 9/00* | (2006.01) | |
| *A61K 45/06* | (2006.01) | |
| *A61M 25/00* | (2006.01) | |

(52) U.S. Cl.
CPC ........ *A61K 31/4015* (2013.01); *A61K 9/0085* (2013.01); *A61M 25/0067* (2013.01); *A61K 9/0019* (2013.01); *A61K 45/06* (2013.01)

(58) Field of Classification Search
CPC .............. A61K 31/4015; A61K 9/0019; A61K 9/0085; A61K 45/06; A61P 25/08; A61M 25/0067

See application file for complete search history.

(56) References Cited

U.S. PATENT DOCUMENTS

| 4,943,639 A | 7/1990 | Gobert | |
|---|---|---|---|
| 2005/0090548 A1* | 4/2005 | Hildebrand .......... | A61K 31/197 514/561 |
| 2019/0151239 A1 | 5/2019 | Abrams et al. | |

FOREIGN PATENT DOCUMENTS

| CN | 105412007 A | 3/2016 |
|---|---|---|
| CN | 105477012 A | 4/2016 |
| CN | 108403626 A | 8/2018 |
| EP | 2878296 A1 | 3/2015 |
| WO | 2007084541 A1 | 7/2007 |
| WO | 2009014762 A1 | 1/2009 |
| WO | 2009151741 A1 | 12/2009 |
| WO | 2018071893 A1 | 4/2018 |
| WO | 2019084038 A1 | 5/2019 |

OTHER PUBLICATIONS

Fang et. al., English translation of CN 108403626 A, publ. Aug. 17, 2018, pp. 1-17 (Year: 2018).*
Muramatsu et. al., Brain & Development, vol. 39, pp. 231-235, publ. 2017 (Year: 2017).*
Liu et. al., Acta Anaesthesiologica Scand., vol. 61, pp. 11-22, publ. Sep. 20, 2016 (Year: 2016).*
Silva et al., Pharmacokinetic Monitoring of Levetiracetam in Portuguese Refractory Epileptic Patients: Effect of Gender; Weight and Concomitant Therapy. Pharmaceutics 2020, 12, 943.
Steinhoff et al., Levetiracetam and brivaracetam: a review of evidence from clinical trials and clinical experience. Ther Adv Neurol Disord 2019, vol. 12: 1-23.
Rambeck et al., Comparison of Brain Extracellular Fluid, Brain Tissue, Cerebrospinal Fluid, and Serum Concentrations of Antiepileptic Drugs Measured Intraoperatively in Patients with Intractable Epilepsy. Epilepsia, 47(4):681-694, 2006.
Zampella B, Patchana T, Wiginton J G, et al. (Sep. 27, 2019) Seizure Prophylaxis in Traumatic Brain Injury: A Comparative Study of Levetiracetam and Phenytoin Cerebrospinal Fluid Levels in Trauma Patients with Signs of Increased Intracranial Pressure Requiring Ventriculostomy. Cureus 11(9): e5784.
Tong, University of London Thesis, The pharmacokinetics and neuropharmacological action of the new antiepileptic drugs vigabatrin and levetiracetam (dated 2007).
Levetiracetam AHFS 28:12.92 (dated May 2013).
Farquhar-Smith and Suzanne Chapman, Neuraxial (epidural and intrathecal) opioids for intractable pain. British Journal of Pain 6(1) 25-35 (2012).
ClinicalTrials.gov Identifier: NCT02899611. A Dose Ranging Pilot Study for Intracerebroventricular (ICV) Delivery of Valproate in Subjects With Temporal Seizures. First Posted Sep. 14, 2016.
Public Release: Apr. 3, 2019, First clinical trial of reformulated epileptic drug to treat medically refractory epilepsy University of Colorado Anschutz Medical Campus.
Flowonix® Medical Inc. And Cerebral Therapeutics Announce World-First Clinical Trial Delivering Medication Directly Into the Brain for Patients With Refractory Epilepsy Implantable programmable drug pump in First use for new experimental application News Provided by Flowonix Medical Inc. Mar. 14, 2017, 16:33 ET.
Tong et al., A microdialysis study of the novel antiepileptic drug levetiracetam: extracellular pharmacokinetics and effect on taurine in rat brain. British Journal of Pharmacology (2001) 133, 867-874.
De Smedt et al., Levetiracetam: The Profile of a Novel Anticonvulsant Drug—Part 1: Preclinical Data. CNS Drug Reviews vol. 13, No. 1, pp. 43-56 2007.
De Smedt et al., Levetiracetam: Part II, the Clinical Profile of a Novel Anticonvulsant Drug. CNS Drug Reviews vol. 13, No. 1, pp. 57-78 2007.
Schmidt, Drug treatment of epilepsy: Options and limitations. Epilepsy & Behavior 15 (2009) 56-65.
Mbizvo GK, Dixon P, Hutton JL, Marson AG. Levetiracetam add-on for drug-resistant focal epilepsy: an updated Cochrane Review. Cochrane Database of Systematic Reviews 2012, Issue 9. Art. No. CD001901.

(Continued)

*Primary Examiner* — Sarah Pihonak
(74) *Attorney, Agent, or Firm* — Clark G. Sullivan

(57) ABSTRACT

Methods of treatment, pharmaceutically acceptable solutions, and implantable devices are provided for the intrathecal treatment of AED-resistant seizures using levetiracetam.

20 Claims, 1 Drawing Sheet

(56) References Cited

OTHER PUBLICATIONS

Lioresal® Intrathecal (baclofen injection) (first approved Nov. 7, 1996).

Scheffer et al., ILAE classification of the epilepsies: Position paper of the ILAE Commission for Classification and Terminology. Epilepsia, 58(4):512-521, 2017.

Fisher et al., Operational classification of seizure types by the International League Against Epilepsy: Position Paper of the ILAE Commission for Classification and Terminology. Epilepsia, 58(4):522-530, 2017.

Fisher et al., New Routes for Delivery of Anti-Epileptic Medications. Acta Neurol Taiwan 2006;15:225-231.

Doheny et al., A comparison of the efficacy of carbamazepine and the novel anti-epileptic drug levetiracetam in the tetanus toxin model of focal complex partial epilepsy. British Journal of Pharmacology (2002) 135, 1425 ± 1434.

Doheny et al., Blood and cerebrospinal fluid pharmacokinetics of the novel anticonvulsant levetiracetam (ucb L059) in the rat. Epilepsy Research 34 (1999) 161-168.

Gonzalez-Darder et al., Intrathecal Antiepileptic Drugs in Experimental Epilepsy. Stereotact Funct Neurosurg 1991; 57:146-155.

Dan et al., Consensus on the appropriate use of intrathecal baclofen (ITB) therapy in paediatric spasticity. European Journal of Pediatric Neurology 14 (2010) 19-28.

Cook et al., Anti-seizure therapy with a long-term, implanted intra-cerebroventricular delivery system for drug resistant epilepsy: A first-in-man study. EClinicalMedicine 22(2020)100326.

Bottros et al., Current perspectives on intrathecal drug delivery. Journal of Pain Research 2014:7 615-626.

Bennewitz et al., Nanotechnology for Delivery of Drugs to the Brain for Epilepsy. vol. 6, 323-336, Apr. 2009. The American Society for Experimental NeuroTherapeutics, Inc.

Barcia et al., Intraventricular and Intracerebral Delivery of Anti-epileptic Drugs in the Kindling Model. vol. 6, 337-343, Apr. 2009. The American Society for Experimental NeuroTherapeutics, Inc.

Alisky, Pregnancy outcomes for women with epilepsy and bipolar disorder could be improved with intraventricular or intrathecal medication administration. Correspondence / Medical Hypotheses 73 (2009) 1072-1080.

Abou-Khalil, Levetiracetam in the treatment of epilepsy. Neuropsychiatric Disease and Treatment 2008:4(3) 507-523.

Abrams, Feasibility of Delivery of Anti-Epilepsy Medications into the Cerebrospinal Fluid (10802). Abstracts from the 19th Annual North American Neuromodulation Society Meeting (NANS) Las Vegas, NV, USA Dec. 10-13, 2015.

Goncalves et al; Nose-to-Brain Delivery of Levetiracetam After Intranasal Administration to Mice; International Journal of Pharmaceutics; Elsevier; 2019; 329-339.

Sintetica S.A.; International Application No. PCT/IB2020/057556 filed Aug. 12, 2020; International Search Report and Written Opinion; ISA/EP; dated Nov. 27, 2020; 16pp.

* cited by examiner

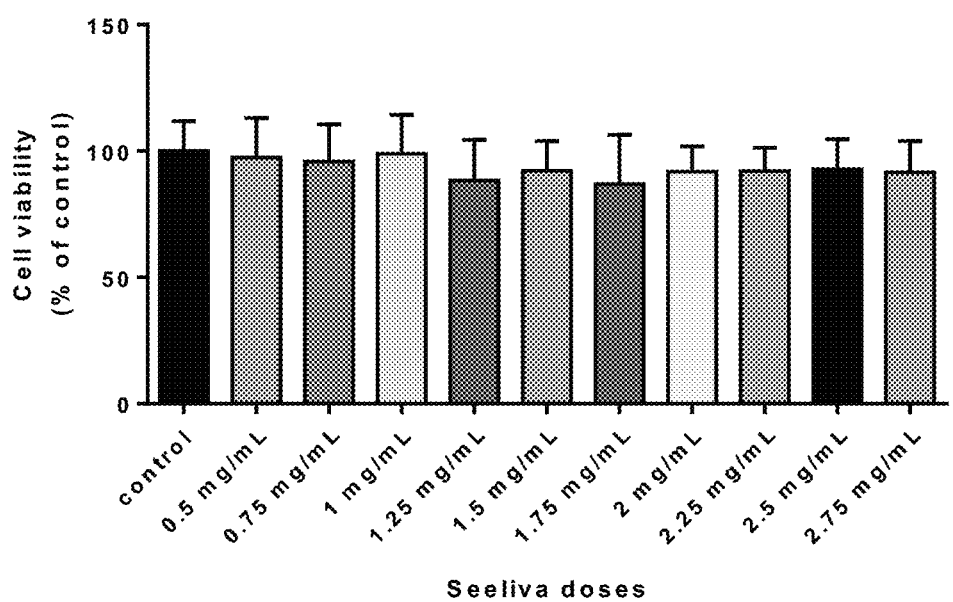

INTRATHECAL ADMINISTRATION OF LEVETIRACETAM

FIELD OF THE INVENTION

The present invention relates to methods for reducing or preventing seizures in patients, particularly seizures that are resistant to orally and systemically administered anti-epileptic drugs ("AEDs"). The methods are particularly well adapted to the treatment of debilitating seizure clusters, by intrathecally administering levetiracetam using implantable reservoir-fed pumps.

BACKGROUND OF THE INVENTION

Since at least the 1970's, researchers have been investigating the potential benefits from administering medications directly to the central nervous system, i.e. into the intracerebroventricular space ("ICV"), into the intra-thecal space, and more generally into the spinal axis. Several therapies have been developed for the treatment of chronic pain and chronic muscle spasms using morphine, ziconitide, and baclofen, under the trade names Infumorph®, Prialt®, and Lioresal®, respectively. Each of these drugs is infused into the cerebral spinal fluid ("CSF") via a SynchroMed®-II implantable pump manufactured by Medtronic (Minneapolis, Minn.), or a similar device.

The SynchroMed®-II implantable pump and similar pumps are surgically implanted through a lumbar puncture in the abdomen. The device is implanted chronically and is expected to remain in place for many years because of the chronic nature of the pain or spasticity. The programmable delivery system offers additional patient benefits because it only needs to be filled every few months, and a programmable pump allows complex dosing options.

More recently researchers have investigated the potential for administering antipsychotic drugs and anti-epileptic drugs ("AEDs") directly to the central nervous system. In 1991 Gonzàlez-Darder et al. reported a study on the effects of intrathecal administered sodium valproate, phenobarbital sodium, and midazolam on electroshock-induced convulsions in an experimental rat model. See Gonzàlez-Darder J M, Gómez-Cárdenas E, Guerrero M, Segura-Pastor D, Gil-Salú J L. Intrathecal antiepileptic drugs in experimental epilepsy. Stereotact Funct Neurosurg 1991; 57(3):147-55. More recently, Stevens et al. proposed intra-thecal and ICV administration of various AEDs and anti-psychotic drugs for the treatment of epilepsy and other neurological disorders. See Stevens K E, Abrams D J, Anchordoquy T, Bunch R. Central administration of stable formulations of therapeutic agents for CNS conditions. WO 2009/014762 (2009).

Numerous challenges, both known and unknown, confound any effort to administer a drug centrally, particularly intrathecally. For example, Fisher et al. report that intrathecally administered drugs "may not penetrate ventricular fluids." Fisher R S, Chen D K. New routes for delivery of anti-epileptic medications. Acta Neurol Taiwan 2006; 15(4): 225-31. Bennewitz et al. report that drugs localize in ependymal cells lining the ventricles when administered intrathecally, and as a consequence might not even reach the site of focal seizures. Bennewitz M F and Saltzman W M. Nanotechnology for Delivery of Drugs to the Brain for Epilepsy. Neurotherapeutics, Vol. 6, 323-336, April 2009. Because of these limitations, most recent efforts at CNS delivery have focused on administering the AED in close proximity to the intended site of action, as through intracerebroventricular delivery. See Stevens et al., supra, WO 2009/014762 (2009).

Numerous AEDs have been developed for the treatment of seizures over the years targeting various molecular pathways, including levetiracetam, sold under the trade name Keppra® by UCB Pharma (Smyrna, Ga.). The injectable dosage form of Keppra® is approved in the United States for adjunctive therapy, as an alternative when oral administration is temporarily not feasible, in the treatment of: (i) partial onset seizures in patients 1 month of age and older with epilepsy, (ii) myoclonic seizures in patients 12 years of age and older with juvenile myoclonic epilepsy, and (iii) primary generalized tonic-clonic seizures in patients 6 years of age and older with idiopathic generalized epilepsy.

Treatment-resistant seizures are particularly problematic affecting approximately one third of epilepsy patients. In 2010, the International League Against Epilepsy published a consensus definition of drug-resistant epilepsy that encompasses two hierarchical levels. Level 1 provides a general scheme to categorize response to interventions as seizure freedom, treatment failure, or undetermined, on the basis of standard criteria. Level 1 provides the basis for Level 2 determinations, which form the core definition of drug-resistant epilepsy "as a failure of at least two tolerated, appropriately chosen and used" AED regimens "to achieve sustained freedom of seizures." According to the "rule of three" for calculating confidence intervals for zero events, "sustained seizure freedom" requires that the patient be seizure-free for at least three-times the longest inter-seizure interval before the intervention, or at least 12 months, whichever is greater.

Seizure clusters can be the most debilitating epileptic event and the most difficult to treat, particularly if they occur regularly. According to the Epilepsy Foundation, there is no definitive clinical definition for a cluster or series of seizures although, at the simplest level, a seizure cluster is a closely grouped series of seizures. Studies examining clinically defined seizure clustering patterns have used varying empiric definitions, including two to four seizures per <48 hours; 3 seizures per 24 hours; or two generalized tonic-clonic or three complex partial seizures in 4 hours. Nonspecific definitions, such as "those having several convulsions within a day or two," have also been described. In a large randomized controlled trial of treatment for acute repetitive seizures, the condition was defined as "multiple seizures occurring with a 24 period for adults or 12 hour period for children, with a pattern distinguishable from the usual seizure pattern."

Accordingly, it is an object of the present invention to treat both patients who experience seizures that are resistant to treatment by systemically administered levetiracetam and other anti-epilepsy drugs, cluster seizures, and other frequent debilitating seizures.

A further object of the present invention to provide methods for treating such treatment-resistant seizures using centrally administered anti-epileptic drugs, particularly intrathecally administered levetiracetam.

Another object of the present invention is to provide methods for treating treatment-resistant seizure clusters, particularly debilitating regularly occurring seizures and seizure clusters, using centrally administered AEDs, particularly intrathecally administered levetiracetam.

Still another object of the present invention is to provide pharmaceutically acceptable liquid solutions of levetiracetam that are suitable for central administration to epilepsy patients, which are particularly suitable for intrathecal administration through an implantable reservoir-fed pump.

SUMMARY OF INVENTION

The inventors have unexpectedly discovered that levetiracetam administered intrathecally by the methods of the current invention is able to treat seizures, even in patients who suffer frequent debilitating seizures. The methods of the present invention are particularly useful for preventing seizures that are resistant to systemically administered levetiracetam, even in patients who frequently suffer multiple debilitating seizures. Thus, in a first principal embodiment, the invention provides a method of treating or preventing seizures in a human patient in need thereof comprising intrathecally administering to said patient a therapeutically effective amount of a pharmaceutically acceptable solution comprising levetiracetam or a pharmaceutically acceptable salt thereof, wherein said seizures are resistant to treatment by systemically administered levetiracetam.

The methods of the present invention are also useful for preventing seizures that are resistant to other systemically administered AEDs. Thus, in a second principal embodiment the invention provides a method of treating or preventing seizures in a human patient in need thereof comprising intrathecally administering to said patient a therapeutically effective amount of a pharmaceutically acceptable solution comprising levetiracetam or a pharmaceutically acceptable salt thereof, wherein said seizures are resistant to treatment by two or more systemically administered anti-epileptic drugs.

The methods also can be practiced using other central methods of administration, to treat seizures that are resistant to treatment by oral or systemic levetiracetam and other anti-epileptic drugs. Thus, in a third principal embodiment the invention provides a method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by systemically administered levetiracetam.

A fourth principal embodiment the invention provides a method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by two or more systemically administered anti-epileptic drugs.

Still another embodiment is directed toward the treatment of frequent debilitating seizures using intrathecal administration, regardless of whether the seizures are resistant to treatment by systemically administered AEDs Thus, in a fifth principal embodiment, the invention provides a method of treating or preventing frequent debilitating seizures in a human patient in need thereof comprising intrathecally administering to said patient a therapeutically effective amount of a pharmaceutically acceptable solution comprising levetiracetam or a pharmaceutically acceptable salt thereof.

Still further embodiments are directed to pharmaceutically acceptable solutions of levetiracetam useful for practicing the methods of the present invention, which are substantially isotonic, and unaffected by tonicity affecting compounds such as sodium chloride and other halide salts, particularly in quantities that render the solution non-isotonic (i.e. outside the range of 270-330 mOsm/kg). Thus, in a sixth principal embodiment the invention provides a substantially isotonic pharmaceutically acceptable solution comprising from 2.5 to 60 mg/ml of levetiracetam in water, buffered at a pH of from 5 to 7.

Additional advantages of the invention are set forth in part in the description which follows, and in part will be obvious from the description or may be learned by practice of the invention. The advantages of the invention will be realized and attained by means of the elements and combinations particularly pointed out in the appended claims. It is to be understood that both the foregoing general description and the following detailed description are exemplary and explanatory only and are not restrictive of the invention, as claimed.

BRIEF DESCRIPTION OF THE FIGURES

The accompanying drawings, which are incorporated in and constitute a part of this specification, illustrate several embodiments of the invention and together with the description serve to explain the principles of the invention.

FIG. 1 is a bar graph depicting cell viability of murine cells at different concentrations of levetiracetam in the MTT test described in Example 3. Results are reported as mean±Standard deviation.

DETAILED DESCRIPTION

Definitions and Use of Terms

As used in this specification and in the claims which follow, the singular forms "a," "an" and "the" include plural referents unless the context clearly dictates otherwise.

As used in this specification and in the claims which follow, the word "comprise" and variations of the word, such as "comprising" and "comprises," means "including but not limited to," and is not intended to exclude, for example, other additives, components, integers or steps. When an element is described as comprising a plurality components, steps or conditions, it will be understood that the element can also be described as comprising any combination of such plurality, or "consisting of" or "consisting essentially of" the plurality or combination of components, steps or conditions.

"Therapeutically effective amount" means that amount which, when administered to a human for supporting or affecting a metabolic process, or for treating or preventing a disease, is sufficient to cause such treatment or prevention of the disease or supporting or affecting the metabolic process.

When ranges are given by specifying the lower end of a range separately from the upper end of the range, or specifying particular numerical values, it will be understood that a range can be defined by selectively combining any of the lower end variables, upper end variables, and particular numerical values that is mathematically possible. In like manner, when a range is defined as spanning from one endpoint to another, the range will be understood also to encompass a span between and excluding the two endpoints.

When "drug therapy" is recited, it will be understood that the therapy can be accomplished through any suitable route of administration using any acceptable dosage form, and that the drug can be administered as the free base, a salt, or an ester or other prodrug moiety.

When used herein the term "about" will compensate for variability allowed for in the pharmaceutical industry and inherent in products in this industry, such as differences in product strength due to manufacturing variation and time-induced product degradation. The term allows for any variation which in the practice of good manufacturing practices would allow the product being evaluated to be considered therapeutically equivalent or bioequivalent in humans to the recited strength of a claimed product. Whenever a number is recited herein, it will be understood that the number can be preceded by the term "about."

In the context of the present invention insofar as it relates to any of the disease conditions recited herein, the term "treatment" means to reduce the occurrence of a symptom or condition, or to relieve or alleviate at least one symptom associated with such condition, or to slow or reverse the progression of such condition, or to manage or affect the metabolic processes underlying such condition. Within the meaning of the present invention, the terms also denote to arrest, delay the onset (i.e., the period prior to clinical manifestation of a disease) and/or reduce the risk of developing or worsening a disease.

The phrase "acceptable" as used in connection with compositions of the invention, refers to molecular entities and other ingredients of such compositions that are physiologically tolerable and do not typically produce untoward reactions when administered to a subject (e.g., a mammal such as a human).

An anti-epileptic drug or "AED" refers to any medication shown to reduce the frequency of seizures in a patient with epilepsy. Exemplary AEDs within the scope of the present invention include carbamazepine, tiagabine, levetiracetam, lamotrigine, pregabalin, fenfluramine, gabapentin, phenytoin, topiramate, oxcarbazepine, valproate, valproic acid, zonisamide, perampanel, eslicarbazepine acetate, lacosamide, vigabatrin, rufinamide, fosphenytoin, ethosuximide, phenobarbital, diazepam, lorazepam, clonazepam, clobazam, ezogabine, felbamate, primidone, acetazolamide, brivaracetam, clorazepate, ethotoin, mephenytoin, methsuximide, trimethadione, bumetanide, and adenosine. In the methods of the current invention, the seizures can be resistant to one, two, three, four, or more of any combination of the foregoing AEDs.

A stable formulation can be defined as a formulation that satisfies the chemical stability requirements described in International Conference on Harmonization Guideline ICH Q1A(R2) (February 2003).

"Systemic" administration is a route of administration of medication, nutrition or other substance into the circulatory system so that the entire body is affected. Administration can take place via enteral administration (absorption of the drug through the gastrointestinal tract, for example, when orally administered) or parenteral administration (generally injection, infusion, or implantation). Systemic administration should be distinguished from intrathecal or central administration where only the central nervous system is affected.

Intrathecal administration refers to the direct injection of medication from outside the body into the cerebrospinal fluid that occupies the subarachnoid space in the central nervous system, via a catheter, needle or other suitable injection device. Intrathecal administration can thus be distinguished from systemic administration and epidural administration. Intrathecal administration can be used to deliver medication to the cerebrospinal fluid at any location in the central nervous system, and will be referred to herein as spinal intrathecal injection when the administration occurs in the spine, and intracranial intrathecal delivery when the administration occurs in the brain.

Seizure types and definitions can be found in the International League Against Epilepsy (ILAE) Classification of Epileptic Seizures (2017), published by RS Fisher et al., Operational classification of seizure types by the International League Against Epilepsy ("ILAE"): Position Paper of the ILAE Commission for Classification and Terminology. Epilepsia, 58(4):522-530, 2017 ("ILAE 2017 Position Paper").

Whenever a seizure is referred to herein, it will be understood to encompass any of the seizure types described in the ILAE 2017 Position Paper. It will also be understood that the seizure is preferably a focal seizure unless the seizure is expressly defined as another type. It will also be understood that the seizures most suitable for treatment are clinically meaningful or disabling.

Levetiracetam refers to (−)-(S)-α-ethyl-2-oxo-1-pyrrolidine acetamide and any of its pharmaceutically acceptable salts, represented by the following chemical structure:

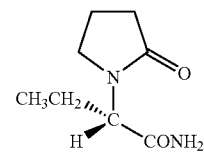

Principal Embodiments

In a first principal embodiment, the invention provides a method of treating or preventing seizures in a human patient in need thereof comprising intrathecally administering to said patient a therapeutically effective amount of a pharmaceutically acceptable solution comprising levetiracetam or a pharmaceutically acceptable salt thereof, wherein said seizures are resistant to treatment by systemically administered levetiracetam.

In a second principal embodiment the invention provides a method of treating or preventing seizures in a human patient in need thereof comprising intrathecally administering to said patient a therapeutically effective amount of a pharmaceutically acceptable solution comprising levetiracetam or a pharmaceutically acceptable salt thereof, wherein said seizures are resistant to treatment by two or more systemically administered anti-epileptic drugs.

In a third principal embodiment the invention provides a method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by systemically administered levetiracetam.

In a fourth principal embodiment the invention provides a method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by two or more systemically administered anti-epileptic drugs.

In a fifth principal embodiment the invention provides a method of treating or preventing frequent debilitating seizures in a human patient in need thereof comprising intrathecally administering to said patient a therapeutically effective amount of a pharmaceutically acceptable solution comprising levetiracetam or a pharmaceutically acceptable salt thereof.

Still further embodiments are directed to pharmaceutically acceptable solutions of levetiracetam useful for practicing the methods of the present invention. Thus, in a sixth principal embodiment the invention provides a substantially isotonic pharmaceutically acceptable solution comprising from 2.5 to 60 mg/ml of levetiracetam in water, buffered at a pH of from 5 to 7.

Exemplary Treatment Methods

The methods herein are particularly well adapted to intrathecal administration of levetiracetam, although they also can be used more generally in other central administration techniques. By "central" administration is meant physical administration targeted at the central nervous system. Thus, the methods described herein generally comprise central delivery of levetiracetam, including the pharmaceutical compositions described herein, to a human patient in need thereof. The solution can be administered intrathecally through spinal or lumbar delivery into the subarachnoid space; through intracranial delivery (administration into the brain parenchyma); intracerebroventricular (ICV) delivery (administration into the cerebral ventricles), etc.

The levetiracetam can be administered acutely or chronically, and may be via injection, infusion, pump, implantable pump, etc. A preferred method of administration is chronic intrathecal administration to the spine or brain. In one particular embodiment the solution is injected through a catheter tip inserted into the thoracic or cervical region of the spinal column of said patient. In another embodiment, the solution is intrathecally injected through a catheter tip inserted into the thoracic or cervical region of the spinal column of said patient, preferably the cervical region. Thus, the solution is preferably injected between the C1 and C7 vertebrae, between the C1 and C5 vertebrae, between the C1 and C3 vertebrae, or at the C1 vertebrate (i.e. immediately above or below the C1 vertebrae) when intrathecally administered.

Alternatively, the intrathecal administration occurs in the brain, via intracranial intrathecal administration. The catheter can be positioned in any of the temporal lobes, with the hippocampus the preferred anatomical target.

Generally the total daily dose can be adjusted based on patient response, and a therapeutically effective dose arrived at within 2-3 months or even 7-10 days when monitoring and adjustment is more aggressive. The total daily dose of levetiracetam when given by intrathecal (spinal or intracranial) or central administration will typically range from 0.1 to 150 mg/day, from 0.5 to 60 mg/day, or from 2 to 40 mg/day. Alternatively, the total daily dose of levetiracetam when given by intrathecal (spinal or intracranial) or central administration can range from 20 to 1000 mg/day, from 50 to 500 mg/day, or from 75 to 350 mg/day. In still further alternatives, the intrathecal (spinal or intracranial) or centrally administered dose can range from 50 to 250 mg/day, from 250 to 500 mg/day, from 500 to 750 mg/day, from 750 to 1000 mg/day, from 50 to 175 mg/day, from 175 to 300 mg/day, from 300 to 425 mg/day, from 425 to 550 mg/day, from 500 to 625 mg/day, from 625 to 750 mg/day, from 750 to 875 mg/day, or from 875 to 1000 mg/day.

The rate of administration can also be determined volumetrically, and in alternative and/or additional embodiments the levetiracetam is administered at a rate of from 0.05 to 20 ml/day, from 0.1 to 10 ml/day, or from 0.2 to 2 ml/day. Once again, these volumetric ranges apply to intrathecal (spinal or intracranial) or central administration.

The methods of the current invention can be practiced using any of the solutions of the current invention, preferably adapted for use with an implantable pump so that the concentration of the solution and its dosing rate correlate with the volume in the pump's reservoir and the intended frequency of refilling the reservoir.

In another embodiment the solution is administered continuously or intermittently over at least one week, one month, or even two months from a fluid reservoir via an implantable delivery device, before the reservoir must be refilled. In still another embodiment the solution is administered continuously or intermittently over at least one week, one month, or two months via an implantable delivery device, without refilling, at a delivery rate of from 0.5 to 60 mg/day, from 0.1 to 150 mg/day, from 0.5 to 60 mg/day, from 2 to 40 mg/day, from 20 to 1000 mg/day, from 50 to 500 mg/day, or from 75 to 350 mg/day, before the reservoir must be refilled. In still further alternatives, the continuous or intermittent dose can range from 50 to 250 mg/day, from 250 to 500 mg/day, from 500 to 750 mg/day, from 750 to 1000 mg/day, from 50 to 175 mg/day, from 175 to 300 mg/day, from 300 to 425 mg/day, from 425 to 550 mg/day, from 500 to 625 mg/day, from 625 to 750 mg/day, from 750 to 875 mg/day, or from 875 to 1000 mg/day, over at least one week, one month, or two months via an implantable delivery device, without refilling. Once again, these dosing ranges apply to intrathecal (spinal or intracranial) or central administration.

In other embodiments, the methods can be practiced either as monotherapy on in addition to background AED therapy. Thus, in one embodiment, the method is practiced as monotherapy. In other embodiments the method is practiced as add-on therapy to a pre-existing drug regimen comprising one, two, or more anti-epileptic drugs.

Epilepsies

The methods of the present invention can be used to treat any individual who suffers from epilepsy. For use herein, unless clearly indicated otherwise, "an individual" intends any mammal, but preferably is a human. The individual may have been diagnosed with, is suspected of having, or is at risk of developing an indication for which treatment with an AED is beneficial, such as epilepsy.

In addition, the methods of the present invention can be used to treat any individual "in need thereof," including individuals who have a condition or disease for which treatment with an AED is beneficial, such as epilepsy, or who are "at risk" for the condition or disease. Methods for the diagnosis of epilepsy, as well as procedures for the identification of individuals at risk for developing epilepsy, are well known to those in the art. Such procedures may include clinical tests, physical examination, personal interviews, and assessment of family history.

In some embodiments, the individual (such as a human) has refractory (i.e. treatment resistant) epilepsy. AEDs Treatment resistance is preferably defined according to the ILAE consensus definition as epilepsy for which there has been "failure of adequate trials of two tolerated and appropriately chosen and used AED schedules (whether as monotherapies or in combination) to achieve sustained seizure freedom." P Kwan et al., Definition of drug resistant epilepsy: consensus proposal by the ad hoc Task Force of the ILAE Commission on Therapeutic Strategies. Epilepsia 2010; 51(6):1069-77. No seizure frequency requirement is necessary to meet this ILAE definition. This allows for those patients with infrequent seizures (e.g. occurring once a year) to still be regarded as drug resistant, which is relevant to the impact seizures have on lifestyle factors such as driving.

In some embodiments, the individual is selected from the population of individuals who are refractory to treatment via oral or systemic administration of a compound for the treatment of epilepsy. In some embodiments, the individual has not responded to 1, 2, 3, 4, or more systemically administered AEDs (administered as separate monotherapies or as combination therapies) for the treatment of epilepsy prior to treatment with a method of the invention. In some embodiments, the individual has seizures that have not been adequately controlled by 1, 2, 3, 4, or more AEDs prior to treatment with a method of the invention. In some embodiments, the individual is selected from the population of individuals who are refractory (i.e. resistant) to treatment via oral or systemic administration of AEDs. In some embodiments, the individual has failed surgical treatment (such as vagus nerve stimulation) or has been determined to not have a surgical option for treatment. In various embodiments, the individual has had at least 1, 2, 3, 4, 5, 6, or more complex partial or generalized tonic-clonic seizures per month for at least 1, 2, 3, 4, 5, 6, or more months prior to treatment with a method of the invention. In one particular embodiment, the individual has not responded to oral or systemic levetiracetam therapy prior to the method of the present invention, potentially in addition to 1, 2, 3, or 4, or more additional AEDs. In yet another embodiment, the individual has not responded to 1, 2, 3, 4, or more systemically administered AEDs.

Resistance to treatment can also be defined based on the reduction in seizures—preferably focal (i.e. partial) seizures—achieved by the patient's background AEDs. In one embodiment, the resistance to treatment is defined as the failure to achieve sustained seizure freedom. In another embodiment, the resistance to treatment is defined as an inability to reduce the frequency of seizures by more than 20% or 50% or 80% compared to pre-treatment frequency. In other embodiments, the resistance to treatment is defined as the failure to reduce the frequency of seizures to less than two or five seizures per month.

Still further embodiments can be based on the patient's seizure frequency prior to initiating the levetiracetam therapy, again preferably based on the measurement of focal (i.e. partial) seizures. Thus, in one embodiment the patient has suffered during the three months preceding initiation of the levetiracetam treatment of the current invention, on average, four, six, or eight or more focal seizures per month. In an alternative or additional embodiment, the patient has suffered in the three months preceding initiation of said method no period longer than 30 days with less than two, four, or six focal seizures. In yet another alternative or additional embodiment, the patient has not suffered in the three months preceding initiation of said method more than 10 focal seizures in one day or more than 300 focal seizures in any one month period.

Particularly preferred embodiments are defined by one of the following conditions:

the patient suffers cluster seizures according to one of the definitions given in the background of this document.

the patient suffers cluster seizures according to one of the definitions given in the background of this document and is resistant to treatment via oral or systemic administration of levetiracetam.

the patient suffers focal seizures, either simple or complex.

the patient suffers focal seizures, either simple or complex, and is resistant to treatment via oral or systemic administration of levetiracetam.

the patient suffers general seizures.

the patient suffers general seizures and is resistant to treatment via oral or systemic administration of levetiracetam.

the patient suffers primary generalized tonic-clonic seizures.

the patient suffers primary generalized tonic-clonic seizures and is resistant to treatment via oral or systemic administration of levetiracetam.

These methods can be used to treat any condition for which treatment with an AED is beneficial, particularly levetiracetam. By "treatment" or "treating" is meant an approach for obtaining a beneficial or desired result, including clinical results. For purposes of this invention, beneficial or desired results include, but are not limited to, alleviation or reduction in the number of symptoms (such as seizures) associated with a condition (such as, but not limited to, epilepsy), diminishment of the extent of the symptoms associated with a condition (such as the severity or duration of seizures), delaying the development of a condition, or prevention of a worsening of the symptoms associated with a condition. In some embodiments, treatment with the pharmaceutical compositions disclosed herein is accompanied by no or fewer side-effects than are associated with currently available therapies.

In some embodiments, any of the methods described herein produce a percentage reduction in total seizure frequency of at least about 10, 20, 30, 40, 50, 60, 70, 80, 90, 95, or 100% compared to the seizure frequency in the same individual prior to treatment or compared to the seizure frequency in other individuals not receiving the treatment. The seizure frequency is preferably based on the number of seizures experienced in any given month.

Exemplary Implantable Pumps

In certain preferred embodiments, the administration is via an implantable pump. By way of non-limiting example, devices such as those disclosed in U.S. Patent Publication 2004/0133184, which is herein incorporated by reference in its entirety, may be used in addition to other similar devices. Continuous administration may be achieved using an implantable or attachable pump controlled delivery device, such as the SynchroMed-II® pump marketed by Medtronic, Inc. (Minneapolis, Minn.). Other implantable pumps suitable for practicing the present invention are manufactured by Flowonix Medical, Inc. (Mt. Olive, N.J.) under the Prometra® line of programmable pumps, and tricumed Medizintechnik GmbH (Kiel Germany).

Certain embodiments involve using an implanted catheter pump system for at least one month, at least about two months, at least about three months, at least about 4 months, at least about 5 months, at least about 6 months, etc. of chronic intrathecal administration. These pumps are implanted in a 45-minute procedure performed by anesthesiologists, neurosurgeons, and general surgeons. The pump is located in the abdomen and the catheter is placed into the CSF through a spinal tap. The catheter lies outside the spinal cord tissue and medication is administered from the tip of the catheter.

The pump drug reservoir is designed for refill, typically at an interval of from one month to one year, depending on patient dosing requirements. In clinical practice, a physician (or nursing and physician assistant) will program and refill the pump. Typical follow-up after a pump placement is 1 week, with a second visit 1 month later. Usually patients are seen at a maximum of once per week for programmable dose adjustment in the first two to three months and thereafter every three months unless symptoms or medication side-effects require programming adjustment of the drug dose.

Injection from the implantable pump is typically continuous or intermittent, using a computerized pump preferably to provide a delivery rate of about 1.5 to about 90 mg of levetiracetam per hour depending on the severity of symptoms. CSF concentration can be periodically monitored and the delivery rate adjusted accordingly to provide a steady-state concentration of about 10 to about 500 mcg/ml levetiracetam in the cerebrospinal fluid, from about 50 to about 400 mcg/ml levetiracetam in the cerebrospinal fluid, or from about 100 to about 350 mcg/ml levetiracetam in the cerebrospinal fluid. These concentrations apply to intrathecal delivery including spinal and intracranial delivery.

Pharmaceutical Compositions

One aspect of the invention is drawn to pharmaceutical compositions of levetiracetam suitable for central administration, particularly long term or chronic central administration, using implantable intrathecal pumps. Thus, in one principal embodiment the invention provides a substantially isotonic pharmaceutically acceptable solution of levetiracetam in water, preferably at a pH of from 5 to 7, and an optional pH buffer. In another embodiment the invention provides a pharmaceutically acceptable solution comprising or consisting of from 2.5 to 60 mg/ml of levetiracetam in water, preferably at a pH of from 5 to 7, and an optional pH buffer. In either of the foregoing embodiments, it is preferred that no other ingredients be present in the formulation other than unintended by-products, degradants, and other contaminants, and necessary that the solution be isotonic or substantially isotonic.

In a particularly preferred embodiment, in any of the formulations of the present invention, the levetiracetam remains soluble and stable in the solution for at least about two months at 37° C. By remains "stable" is meant that no more than 1%, 5%, 0.1%, or 0.05% of the levetiracetam is degraded when stored in the reservoir or other storage unit such as a closed vial at 37° C., tested under the conditions prescribed in International Conference on Harmonization Guideline ICH Q1A(R2) (February 2003).

Further it is necessary to maintain substantial physiological isotonicity for the formulations. A solution that is substantially isotonic refers to a solution that is either isotonic (i.e. 270-330 mOsm/kg) or, if falling slightly outside the range of osmolality for an isotonic solution, is not expected to produce any unacceptable toxic effects. Thus, when a solution is referred to as substantially isotonic herein, it will be understood to refer to solutions in the 270-330 mOsm/kg range, solutions slightly outside the 270-330 mOsm/kg range that are not expected to result in unacceptable toxicity, or simply solutions within approximately 10% or 15% of the range of osmolality (i.e. 243-363 mOsm/kg or 229-380 mOsm/kg). In another embodiment, a "substantially isotonic solution" will refer to an aqueous solution of levetiracetam at a levetiracetam concentration of from 2.5 to 60 mg/ml with no other solutes such as sodium chloride or other halide salts affecting the tonicity present in the solution, other than pH adjusting agents and buffering agents.

Sodium chloride and other halide salts that affect the tonicity of the solution are preferably omitted from the formulations and unnecessary because levetiracetam itself yields an isotonic (or slightly above isotonic) formulation in the formulations of the present invention. The following table gives the osmolality of various concentrations of levetiracetam in water:

| Levetiracetam conc. (mg/ml) | Osmolality (mOsm/kg) |
|---|---|
| 2.75 | 16 |
| 45 | 262 |
| 50 | 292 |
| 60 | 348 |
| 65 | 377 |

The pH of the formulation can range from 3 to 7, from 5 to 7, from 5 to 6, from 6 to 7, from 6.2 to 7, or from 6.5 to 7, but preferably ranges from 5.2 to 5.8.

The solutions of the present invention preferably have a levetiracetam concentration of from 2.5 to 60 mg/ml, but the levetiracetam concentration also can range from 10 to 60 mg/ml, from 20 to 60 mg/ml, from 30 to 60 mg/ml, or from 40 to 60 mg/ml, depending on the dose required to deliver a therapeutically effective amount and the volumetric delivery rate desired during administration.

When a pH buffer is employed, the buffer preferably comprises acetic acid and sodium acetate in quantities necessary to achieve the desired pH (i.e. 5-7, 5-6, 5.2-5.8, 6-7, 6.2-7, or 6.5-7). In a particularly preferred embodiment, the solutions of the present invention are substantially isotonic and buffered at a pH of from 5 to 6, in the absence of sodium chloride or another halide salt. In a still further embodiment, the solutions of the present invention are buffered at a pH of from 5.2 to 5.8 with a buffer comprising acetic acid and sodium acetate, preferably in the absence of sodium chloride or another halide salt.

In still further defined embodiments:
the solution comprises from 2.5 to 60 mg/ml, from 10 to 60 mg/ml, or from 40 to 60 mg/ml of levetiracetam in water and an optional pH buffer
the solution is a substantially isotonic solution comprising from 2.5 to 60 mg/ml, from 10 to 60 mg/ml, or from 40 to 60 mg/ml of levetiracetam in water and an optional pH buffer;
the solution is a substantially isotonic solution comprising from 2.5 to 60 mg/ml, from 10 to 60 mg/ml, or from 40 to 60 mg/ml of levetiracetam in water buffered at a pH of from 5 to 7;
the said solution is a substantially isotonic solution comprising from 2.5 to 60 mg/ml, from 10 to 60 mg/ml, or from 40 to 60 mg/ml of levetiracetam in water buffered at a pH of from 5 to 7, wherein said buffer comprises acetic acid and sodium acetate; or
the solution is a substantially isotonic solution comprising from 2.5 to 60 mg/ml, from 10 to 60 mg/ml, or from 40 to 60 mg/ml of levetiracetam in water buffered at a pH of from 5 to 7, in the absence of sodium chloride or another halide salt.

EXAMPLES

In the following examples, efforts have been made to ensure accuracy with respect to numbers (e.g., amounts, temperature, etc.) but some errors and deviations should be accounted for. The following examples are put forth so as to provide those of ordinary skill in the art with a complete disclosure and description of how the methods claimed herein are made and evaluated, and are intended to be purely exemplary of the invention and are not intended to limit the scope of what the inventors regard as their invention.

Example 1. Exemplary and Comparative Formulations

Table 1 provides an exemplary formulation of levetiracetam of the current invention ready to use without further dilution or modification. Table 1 also describes the formulation of commercially available 5 ml vials of Keppra®, and the formulation of Keppra® injection after dilution according to the drug's FDA-approved prescribing information.

TABLE 1

| Invention Formulation 1 | Keppra ® (5 ml vial) | Keppra ® (diluted)* |
|---|---|---|
| isotonic | hypertonic (~950 mOsm/kg) | isotonic (270-330 mOsm/kg) |
| 50 mg/ml levetiracetam | 100 mg/ml levetiracetam | 5-15 mg/ml levetiracetam |
| 0.0 mg/ml NaCl | 9 mg/ml NaCl | ~0.009 mg/ml NaCl (assumes dilution in 100 ml 0.9% saline) |
| 0.68 mg/ml sodium acetate trihydrate | 1.64 mg/ml sodium acetate trihydrate | ~0.0164 mg/ml sodium acetate trihydrate (assumed dilution in 100 ml) |
| Glacial acetic acid q.s. to pH 5.5 | Glacial acetic acid q.s. to pH 5.5 | |
| Water q.s. | Water q.s. | Water q.s. |

*According to FDA's approve prescribing information for Keppra injection, from one to three vials (1000 mg/vial) may be diluted in 100 ml saline (0.9%) or dextrose (5%) or lactated ringer's.

Alternative formulations of the present invention are described in Table 2:

TABLE 2

| Invention Formulation 2 | Invention Formulation 3 |
|---|---|
| 0.5% (5 mg/ml) levetiracetam | 0.05% (0.5 mg/ml) levetiracetam |
| Isotonic (289 mOsm/kg) | Isotonic (293 mOsm/kg) |
| 0.68 mg/ml sodium acetate trihydrate | 0.68 mg/ml sodium acetate trihydrate |
| 8 mg/ml NaCl | 8.8 mg/ml NaCl |
| Glacial acetic acid q.s. to pH 5.5 | Glacial acetic acid q.s. to pH 5.5 |

Example 2: Evaluation of Levetiracetam Administered Intrathecally in a Model of Epileptic Rats WAG/Rij male rats (aged 168 to 175 days), a strain originating from Wistar rats, are extensively used as a valid genetic animal model of generalized absence epilepsy (Coenen, A. M 2003). Rats belonging to this strain, at around 2-3 months of life, begin to develop synchronous bilateral discharges (SWD, 7-10 Hz) with peaks at the cortical electroencephalogram (EEG) accompanied by concomitant behavioral episodes of contractions of the vibrissae and accelerated exhalation, head tilt and often eye twitching as in absences that occur in humans.

SWDs are detected in WAG/Rij rats for the first time at around 60-80 days of life. The first SWDs are rare (1 or 2 per hour) and short-lived (1-3 s), the wave is not yet developed, the frequency between the peaks during a discharge is low (4-5 Hz) and the peaks are not very well defined. With age, the number, duration and the frequency of SWDs increase while their amplitude is not changed. The number of animals with SWD also increases according to age: at 3 months of age, 50% of WAG/Rij have fully developed SWD, and at 6 months of age 100% of animals show mature SWD (about 16-20 hour) with a frequency of about 8 Hz and average duration of about 5 seconds. After 6 months of life, there is still an age-dependent increase in the number of SWDs per hour and average duration.

On arrival, WAG/Rij rats were acclimatized at a constant temperature of 20-24° C., with light cycles of 12 hours and with ad libitum access to food and water. At the end of the acclimatization period, the rats were implanted with 2 mL mini-pumps according to the following surgical procedures.

1. Clean the operating table with ethanol 70% and cover with sterile drapes to position the Stereotax.
2. Start gaseous anesthesia (isoflurane 4% and $O_2$ at 0.4 L/min) and direct the flux in anesthesia room. Position the rat in the anesthesia room.
3. Shave the anaesthetized rat from the upper part of the shoulder up to the eyes then place the animal on the Sterotax. Insert mouth and nose in the cone supplying isoflurane to guarantee anesthesia maintenance.
4. Fix the head of the rat with the bars in the ears.
5. Disinfect the surgical field by cleaning the upper part of the head and of the neck with a circular movement from the center of the shaved area moving outwards, first with a piece of cotton dipped in 95% ethanol, and then with a piece of cotton dipped in iodine.
6. Implant the osmotic mini-pumps (Alzet) as follows:
    a. Cut the skin from the neck to the supraorbital area.
    b. Create the subcutaneous pocket for the osmotic pump using blunt scissors with the curve facing upwards and sliding them under the skin at the base of the back of the neck.
    c. Clean the skull with sterile cotton swabs, followed by a piece of cotton dipped in hydrogen peroxide.
    d. Insert the pump subcutaneously at the base of the neck and push it posteriorly towards the left side.
    e. Move the cannula driver to the delivery position and fix it.
    f. Point the tip of the catheter on the bregma and drill a hole in the skull before lowering the catheter. Guide the thin metal catheter through the skull until the base of the plastic cannula is pressed against the top of the skull. Fix the needle-cannula with glass ionomer cement.
    g. Suture the skin and apply a small amount of antibiotic ointment on the head and neck.

To assess the efficacy and safety of levetiracetam administered by intrathecal route ("Seeliva"), 50 WAG/Rij rats were distributed in six experimental groups. Control animals (n=25) were not implanted with the osmotic pump and received no treatment. Twenty-five animals were implanted with osmotic pumps and divided into five treatment groups to receive five different drug concentrations (0.05 mg/ml, 0.1 mg/ml, 1 mg/ml, 2.5 mg/ml and 5 mg/ml). Each concentration was prepared by dilution of Seeliva (50 mg/ml levetiracetam) in a sterile saline solution. The pumps were then filled up to their maximum capacity of 2 ml with the different concentrations and administered at a delivery rate of 2.5 µl/h and a dose of 60 µl/day for 28 days to guarantee the daily doses reported in Table 3.

TABLE 3

| Group | N. of animals | Concentration | Dose mg/day* |
|---|---|---|---|
| 1 | 25 | 0 | 0 |
| 2 | 5 | 0.05 mg/ml | 0.003 |
| 3 | 5 | 0.1 mg/ml | 0.006 |
| 4 | 5 | 1 mg/ml | 0.06 |
| 5 | 5 | 2.5 mg/ml | 0.15 |
| 6 | 5 | 5 mg/ml | 0.30 |

For the whole duration of the experiment, the animals were filmed 24 hours a day. The animals were checked daily by the veterinarian regarding the location of the surgical implant and the state of animal welfare. In addition, the animals were weighed daily at 04:00 p.m.

The clinical status of the animals was assessed using the Score Sheet System (shown in the Table 4) which includes the Rat Grimace Scale (Sotocinal et al. 2011), for the evaluation of signs and behaviors (Table 5) which assigns a score based on severity (from 0-3 relative to the parameter considered).

TABLE 4

| Animal ID: | | Score Day Date/ Time | Score Day Date/ Time | Score Day Date/ Time |
|---|---|---|---|---|
| Body Weight | Normal loss or up to 5% | | | |
| | Loss of 5-10% | | | |
| | Loss over 10% | | | |
| Phenotype (score 0-2 to be attributed to each parameter) | Orbital tightening | | | |
| | Flattening nose/cheeks | | | |
| | Ear changes | | | |
| | Vibrissae movement | | | |
| | Fur condition | | | |
| Physiological State | Normal breath | | | |
| | Slightly fatigued breathing | | | |
| | Considerably fatigued breathing | | | |
| Phycological State | Normal behavior | | | |
| | Slightly subdued behavior | | | |
| | Moderate change in behavior and/or outside of cage mates | | | |
| | Reacts violently/vocalization | | | |
| | TOTAL SCORE | | | |

TABLE 5

| SCORE | DEFINITION |
|---|---|
| 0 | normal condition of the animal |
| 1-2 | slight alteration of the parameters, requires more detailed monitoring |
| 3-5 | average alteration of the parameters, to be considered analgesia |
| 6-10 | significant suffering frequently observed |

Throughout the observation period, rats of control group and rats treated with Seeliva at concentrations of 0.05 mg/ml, 0.1 mg/ml, 1 mg/ml and 2.5 mg/ml had a Score Sheet equal to 0 (condition of normal state). In contrast, rats treated with Seeliva at the 5 mg/ml concentration accumulated a score of 1.0 due to slightly subdued behavior accompanied by abnormal behavior both inside and outside of the cage compatible with a state of low reactivity and vigilance (sleepy tendency).

During the video recording, it was possible to verify that the rats in the control group presented concomitant episodes of contractions of the vibrissae and accelerated breathing, inclination of the head and, often, contractions of the eyes. 100% of the animals in the control group showed these episodes. This result is in line with information in the supplier company fact sheet which reports that around 6 months of life all animals exhibit this symptomatology. From the video recordings we were able to verify that the animals of the control group presented these behavioral episodes lasting 15-18 seconds during the 12 light hours every hour. In the dark hours the duration was similar while the frequency was reduced to one crisis every 1.45/hour.

Rats treated with Seeliva at concentrations of 0.05 mg/ml and 0.1 mg/ml did not show any significant reduction in the number of seizures, when compared to the control group. The group treated with 1 mg/ml presented a reduction of seizures equal to 10% per day but only during the 12 hours of darkness. A significant reduction in the crisis was found in the group of Rats that received the drug at a concentration of 2.5 mg/ml. Specifically, all animals belonging to this experimental group presented a reduction in the number of seizures of 87.4%. In this case, the reduction occurred evenly between 12 light hours and 12 dark hours. The crises that persisted were also slightly reduced in duration. Specifically, the seizures went from a duration of 15-18 seconds to a duration of between 9 and 11 seconds.

The experimental group that received drug at a concentration of 5 mg/ml showed a slightly sleepy state from the beginning of treatment that worsened over time. This experimental group had a crisis reduction of 91.8%, taking into account the adverse event (sleepiness) found. Also in this group the seizure duration was shorter, lasting between 9 and 11 seconds.

28 days after positioning the cannula, the animals were sacrificed. Shortly before the sacrifice, a blood sample was taken from the inferior vena cava for hematological tests. No abnormalities in the hematology were recorded in any group. At sacrifice, the brains of each animal were collected and macroscopically evaluated for potential drug related signs in the cerebral hemispheres. The liver and kidneys were also collected from each animal and evaluated both macroscopically and microscopically to assess any possible drug related toxicity of the drug disposal routes. After 28 days of drug infusion, there were no signs of toxicity in the cerebral hemispheres in any experimental group. Furthermore, macroscopic and microscopic evaluations revealed no significant alterations in the kidneys and in the liver at any dose of drug tested.

Example 3. Study to Evaluate the Toxicity of Levetiracetam in a Murine Neuronal Cell Line To assess the in vitro cytotoxicity of levetiracetam 50 mg/mL ("Seeliva") on motoneurons, NSC-34, a mouse motor neuronal cell line, has been selected for the test. NSC-34 was purchased from Cellutions Biosystems Inc., Cedarlane (Toronto Canada) at passage 27.

To perform the experiment, cells at passage 30 were first thawed and seeded for 3 days in DMEM (Dulbecco's Modified Eagle's Medium) high glucose, supplemented with 1% antibiotics, glutamine and 10% FBS, at 37° C. and 5% $CO_2$ then harvested and reseeded (passage 31) in 96-well plates (100 μl/well) and cultured for 24 hours to reach 70%-80% confluence.

On the day of the experiment, culture medium was withdrawn and replaced with 100 μl of fresh medium containing Seeliva at concentrations ranging from 0.5 to 2.75 mg/ml (8 replicates for each concentration and control). Plates were then incubated for 24 hours, at 37° C. and 5% $CO_2$. After incubation, 10 μl/well MTT (Thiazolyl Blue Tetrazolium Bromide) solution at 5 mg/ml (final concentration in the well: 0.5 mg/ml), were added to each well. The plate was then put back into the incubator at 37° C. and 5% $CO_2$ for 4 hours.

Formazan crystals were then solubilized by the addition of 100 µl/well of 0.1N HCl in isopropanol and a further 1-hour incubation. Absorbance (at 595 nm) was read by a microplate spectrophotometer. Each absorbance value was corrected by the blank (absorbance obtained by reading wells containing only medium, MTT and 0.1N HCl in isopropanol, not seeded with cells) and compared with the absorbance recorded in untreated controls.

The experiment was repeated three times. The higher the absorbance, the higher the viability of the cells. Results obtained in the three separate experiments, reported in FIG. 1, showed that Seeliva was not cytotoxic for mouse motor neuronal cell line NSC-34 in the tested concentration range (0.5-2.75 mg/mL).

Example 4. Study to Evaluate Treatment Efficacy in Humans

Brief Summary

Patients with medically refractory epilepsy will be treated by intrathecal delivery of the levetiracetam solution described in Example 1 using an implantable drug pump system. The dose of levetiracetam will be escalated weekly during a blinded-evaluation period through Day 64 to determine the maximum tolerated dose (MTD). After Day 64, patients can continue for 52 weeks in the open-label evaluation period (non-blinded).

DETAILED DESCRIPTION

Epilepsy patients that are refractory to oral AED treatment have significantly higher mortality, higher morbidity, higher economic costs and diminished quality of life compared to those who suffer from epilepsy that can be adequately controlled with medical management. Current options for refractory patients include neurosurgical brain resection, responsive neurostimulation, and vagal nerve stimulation. None of these options is satisfactory due to the low applicability of surgery for patients with poorly localized or multifocal seizures and the limited success of currently available alternative treatment options.

In this study, patients with medically refractory focal epilepsy will be treated with intrathecal administration of levetiracetam using an implantable drug pump system. The solution is intrathecally injected through a catheter tip inserted into the thoracic or cerebral region of the spinal column of said patient, between the T7 and C1 vertebrae. This is a dose ranging study, with a randomized, double-blind dose escalation component, to establish the dose range of intrathecal levetiracetam delivery.

Clinical assessments, adverse events (AEs), seizure diaries, concomitant medications, blood samples and cerebrospinal fluid (CSF) will be collected and reviewed at designated time points. Magnetic resonance imaging (MM) and electroencephalography (EEG) can also be performed. Subjects should have their surgery, dose changes and pharmacokinetics performed in an inpatient setting.

The intrathecal levetiracetam dose will be escalated stepwise from 5 mg/day to 300 mg/day through Day 64 if tolerated, or stopped earlier upon establishment of a subject's maximum tolerated dose (MTD). The MTD for each subject will be determined based on the highest dose tolerated without experiencing a dose-limiting adverse event (AE). After establishing a subject's MTD, delivery of intrathecal levetiracetam will continue at the MTD through Day 64 of the blinded evaluation period. Subjects and assessing physicians will remain blinded to the treatment dose during the blinded evaluation period. Subjects can continue in the open-label evaluation period (non-blinded) for 52 weeks following the blinded evaluation period.

Study Design

Study Type: Interventional (Clinical Trial)

Estimated Enrollment: 12 participants

Intervention Model: Single Group Assignment

Masking: None (Open Label)

Primary Purpose: Treatment

Official Title: A Dose Ranging Pilot Study to Assess Intrathecal Delivery of Levetiracetam in Subjects With Focal Seizures.

Eligibility Criteria

Ages Eligible for Study: 18 Years to 65 Years (Adult, Older Adult)

Sexes Eligible for Study: All

Inclusion Criteria:

- Subject does not have coagulopathy, ventricular anatomic distortion or abnormally low brain weight or significant volume loss etc. and is approved to have surgery.
- Subject had onset of epilepsy after age 5, had normal brain development up to age 5, and has full scale IQ >70 by testing or functional assessment.
- Subject has brain volume which is not noted to be abnormally small due to atrophy by either the radiologist reading on MRI scan or the treating clinicians (the neurosurgeon) review of the MRI scan.
- Subject has had confirmed epilepsy for a minimum of 1 year, with diagnosis of focal seizures, with or without secondarily generalized seizures, as defined by the International League Against Epilepsy (ILAE) Classification of Epileptic Seizures (1981).
- In the opinion of the investigator, subject has disabling seizures. Disabling refers to seizures that are severe enough to cause injuries, or significantly impair functional ability in domains including employment, psychosocial education and mobility.
- Subject has had a CT or MRI of the brain to rule out progressive structural lesions.
- Subject has had an EEG or video EEG or invasive monitoring within the past 3 yrs consistent with partial seizures (a normal interictal EEG is consistent with partial seizures)
- Subject has previously failed at least 3 AEDs in single or combination use.
- Subject is taking currently approved AED medication(s) and has been on a stable dosing regimen for 1 month prior to screening.
- Subject has completed all investigations necessary to satisfy the Investigator that noninvasive therapies are not likely to be satisfactorily successful.
- For the 3 months before informed consent an average of four or more clinically significant focal seizures, with or without secondary generalization, per month. Only seizures with objectively visible manifestations should be counted. The subject should have no period longer than 30 days in the 3 months prior to enrollment with less than 2 seizures.

Subject has seizures that are distinct, stereotypical events that can be reliably counted, in the opinion of the Investigator, by the subject or caregiver.

Medically refractory for more than one year.

Exclusion Criteria:

Subject has any significant neurologic disease other than epilepsy.

Subject has history, within 12 months prior to screening, of repetitive seizures that cannot be counted.

Subject has pseudoseizures or seizures secondary to illicit drug or alcohol use, neoplasia, active CNS infection, demyelinating disease, degenerative neurological disease, progressive central nervous system disease or metabolic illness.

Subject has been diagnosed with partial motor, primarily generalized seizures or has been diagnosed with psychogenic or nonepileptic seizures in the preceding year.

Subject has had status epilepticus refractory to benzodiazepines and phenytoin within one year prior to screening.

Subject is currently taking neuroleptic medication for behavior control.

Subject is currently implanted with an activated DBS, or RNS device used for treatment of a neurologic or psychiatric condition.

Subject has VNS and the VNS stimulation parameters are not stable. Stable shall be defined such that the stimulation parameters have been changed in the last 4 months or the patient/designee is able to report "magnet swipe" during the same time period.

Subject has had more than 10 seizures in one day or more than 300 seizures in one month within the last year.

In the opinion of the investigator, the subject has a clinically significant or unstable medical condition (including alcohol and/or drug abuse) or a progressive CNS disease.

Throughout this application, various publications are referenced. The disclosures of these publications in their entireties are hereby incorporated by reference into this application in order to more fully describe the state of the art to which this invention pertains. It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The invention claimed is:

1. A method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by systemically administered levetiracetam or two or more systemically administered anti-epileptic drugs other than levetiracetam, wherein the solution is administered continuously or intermittently via an implantable delivery device, at a delivery rate of from 2 to 500 mg levetiracetam per day, and wherein the solution comprises from 2.5 to 60 mg/ml of levetiracetam in water.

2. A method of treating or preventing frequent debilitating seizures in a human patient in need thereof comprising intrathecally administering to said patient a therapeutically effective amount of a pharmaceutically acceptable solution comprising levetiracetam or a pharmaceutically acceptable salt thereof, wherein the solution is administered continuously or intermittently via an implantable delivery device, at a delivery rate of from 20 to 1000 mg levetiracetam per day, and wherein the solution comprises from 2.5 to 60 mg/ml of levetiracetam in water.

3. A substantially isotonic intrathecal pharmaceutically acceptable solution comprising from 2.5 to 60 mg/ml of levetiracetam in water, buffered at a pH of from 5 to 7.

4. The method of claim 1, wherein said levetiracetam is administered via intrathecal intracranial administration.

5. The method of claim 1 wherein said levetiracetam is administered intrathecally through a catheter tip inserted in the cervical region of the spine from the C1 to the C3 vertebrae.

6. The method of claim 1, wherein the solution has a levetiracetam concentration of from 20 to 60 mg/ml.

7. The method of claim 1, wherein the solution is administered continuously or intermittently over at least one month via an implantable delivery device, at a delivery rate of from 20 to 1000 mg levetiracetam per day.

8. The method of claim 1 wherein the levetiracetam is administered at a concentration of from 40 to 60 mg/ml.

9. The method of claim 1 wherein the levetiracetam is administered at a volumetric rate of from 0.05 to 20 ml/day.

10. The method of claim 1, wherein the patient is resistant to treatment via oral or systemic administration of four or more AEDs.

11. The method of claim 1, wherein said solution is a substantially isotonic solution comprising from 2.5 to 60 mg/ml levetiracetam in water and an optional pH buffer.

12. The method of claim 1, wherein said solution is a substantially isotonic solution comprising from 2.5 to 60 mg/ml levetiracetam in water buffered at a pH of from 5 to 7.

13. The method of claim 1, wherein said solution is a substantially isotonic solution comprising from 2.5 to 60 mg/ml levetiracetam in water buffered at a pH of from 5 to 7, in the absence of a tonicity agent.

14. The method of claim 1, wherein said levetiracetam is administered intrathecally, intra-spinally, intracerebroventricularly, or intracranially.

15. The solution of claim 3, comprising from 10 to 60 mg/ml levetiracetam in the absence of a tonicity agent.

16. The solution of claim 3, comprising from 10 to 60 mg/ml levetiracetam, buffered at a pH of from 5.0 to 6.0.

17. The solution of claim 3, buffered at a pH of from 5.2 to 5.8, in the absence of sodium chloride or another halide salt.

18. The solution of claim 3, comprising from 40 to 60 mg/ml levetiracetam, buffered at a pH of from 5.2 to 5.8, wherein said buffer comprises acetic acid and sodium acetate, in the absence of a tonicity agent.

19. A method of treating or preventing seizures in a human patient in need thereof comprising centrally administering to said patient a therapeutically effective amount of a pharmaceutically acceptable solution comprising levetiracetam or a pharmaceutically acceptable salt thereof, wherein said seizures are resistant to treatment by systemically administered levetiracetam or two or more systemically administered anti-epileptic drugs other than levetiracetam, wherein the solution is administered continuously or intermittently via an implantable delivery device, at a delivery rate of from 2 to 500 mg levetiracetam per day, and wherein said levetiracetam is administered intrathecally through a catheter tip inserted in the cervical region of the spine from the C1 to the C3 vertebrae.

20. A method of treating or preventing frequent debilitating seizures in a human patient in need thereof comprising intrathecally administering to said patient a therapeutically effective amount of a pharmaceutically acceptable solution comprising levetiracetam or a pharmaceutically acceptable salt thereof, wherein the solution is administered continuously or intermittently via an implantable delivery device, at a delivery rate of from 20 to 1000 mg levetiracetam per day, and wherein said levetiracetam is administered intrathecally through a catheter tip inserted in the cervical region of the spine from the C1 to the C3 vertebrae.

* * * * *